United States Patent [19]

Takeuchi et al.

[11] Patent Number: 5,091,371
[45] Date of Patent: Feb. 25, 1992

[54] ANTIFUNGAL AND ANTIVIRAL ANTIBIOTIC, BENANOMICIN A 4'''-O-SULFATE OR ITS SALT, AND THE PRODUCTION AND USES THEREOF

[75] Inventors: Tomio Takeuchi, Tokyo; Shinichi Kondo, Yokohama; Daishiro Ikeda, Tokyo, all of Japan

[73] Assignee: Zaidan Hojin Biseibutsu Kagaku Kenkyu Kai, Tokyo, Japan

[21] Appl. No.: 545,696

[22] Filed: Jun. 29, 1990

[30] Foreign Application Priority Data

Mar. 14, 1990 [JP] Japan .................. 2-61254

[51] Int. Cl.$^5$ .................. A61K 31/70; C07H 15/24
[52] U.S. Cl. .................. 514/33; 536/6.4; 536/17.2; 536/17.9; 536/18.1
[58] Field of Search .................. 536/6.4, 17.2, 18.1, 536/17.9; 514/33

[56] References Cited

U.S. PATENT DOCUMENTS 4,393,055 7/1983 Nair et al. .................. 536/18.1
4,973,673 11/1990 Sawada et al. .................. 536/18.1

OTHER PUBLICATIONS

The Merck Index, 9th ed., (1976) No. 7752, p. 1033.

*Primary Examiner*—Johnnie R. Brown
*Assistant Examiner*—Elli Peselev
*Attorney, Agent, or Firm*—Larson and Taylor

[57] ABSTRACT

As a new antifungal and antiviral antibiotic is provided benanomicin A 4'''-O-sulfate or a salt thereof having formula (I)

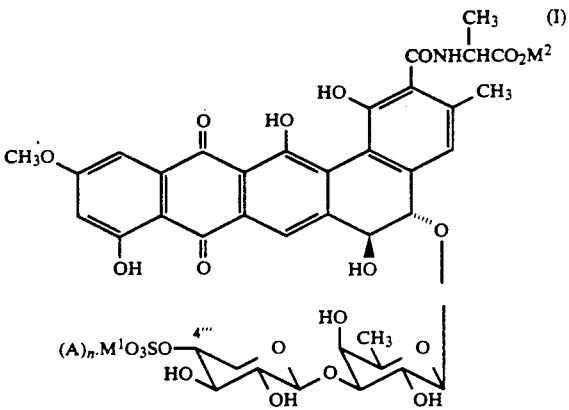

wherein $M^1$ denotes a mono-valent alkali metal atom or a di-valent alkaline earth metal atom or a hydrogen atom and A denotes an organic base; n is zero when $M^1$ is an alkali metal atom or alkaline earth metal atom but n is 1 or zero when $M^1$ is a hydrogen atom, and $M^2$ denotes a hydrogen atom or an alkali metal atom or an alkaline earth metal atom. This new compound is useful as antifungal agent to treat fungal infections in mammals and as antiviral agent to inhibitingly treat HIV.

5 Claims, No Drawings

ANTIFUNGAL AND ANTIVIRAL ANTIBIOTIC, BENANOMICIN A 4'''-O-SULFATE OR ITS SALT, AND THE PRODUCTION AND USES THEREOF

SUMMARY OF THE INVENTION

This invention relates to a new antibiotic, benanomicin A 4'''-O-sulfate or a salt thereof which has an antifungal activity and an antiviral activity and which is useful as a therapeutic antifungal agent and also as an antiviral agent. This invention also relates to pharmaceutical compositions comprising benanomicin A 4'''-O-sulfate or a salt thereof as active ingredient. This invention further relates to a process for the production of benanomicin A 4'''-O-sulfate or a salt thereof.

BACKGROUND OF THE INVENTION

Many antibiotics are already known, but new antibiotic substances are still demanded to be provided as a pharmaceutical agent. Compounds which are already known and similar in their structural feature of the molecule to the new antifungal and antiviral antibiotic, benanomicin A 4'''-O-sulfate or a salt thereof now newly provided by the present inventors include benanomicin A, benanomicin B and dexylosylbenanomicin B (see Japanese patent applications Nos. 277,692/87 and 327,163/87 as laid-open under Japanese patent application publications "Kokai" No. 121,293/83 published on 12 May, 1989 and "Kokai" No. 168,694/89 published on 4 July 1989, respectively, as well as their corresponding European patent application publication No. 0 315 147 A2 published on 10 May 1989 and corresponding U.S. patent application Ser No. 264,888 filed on 31 October 1988) as well as pradimicins A, B and C [Oki et al: "Journal of Antibiotics" 41, 1701-1704 (1988); Tsunakawa et al: "J. Org. Chem." 54, 2532-2536 (1989)].

Hitherto, a variety of antibiotics which are produced by microorganisms are already known. Among the known antibiotics, however, such antifungal antibiotics which can exhibit excellent antifungal effects but a low toxicity to mammals are only few. Accordingly, there is always a demand for discovery and exploitation of a new anti-fungal antibiotic which is useful in the therapeutic treatment of various fungal infections in a mammalian animal, including human.

On the other hand, acquired human immunodeficiency syndrome (sometime called merely as "AIDS") has been found to be a disease which is caused due to human T-cells being infected by a causative virus in human blood. The virus which is causative of the acquired human immunodeficiency syndrome is usually termed as acquired human immunodeficiency syndrome virus which is often abbreviated as HIV. It has been reported that certain known compounds have an antiviral activity against HIV. However, any of these compounds having an antiviral activity against HIV is not necessarily satisfactory as a useful remedial agent for AIDS, and there is a strong outstanding demand to develope and provide such a new drug which shows a low toxicity and a high solubility in water, which can show a high activity to inactivate HIV and which are expectable as a useful medicinal agent for therapeutically or preventively treating AIDS.

According to some inventions which are earlier made by the present inventors, there are provided two antibiotics, benanomicin A and benanomicin B, which each have an antifungal activity and an HIV-inactivating activity, as well as a process for the production of benanomicins A and B by cultivation of an actinomycete strain MH193-16F4 (see the above-mentioned European patent application publication No. 0 315 147 A2 and its corresponding U.S. patent application Ser No. 264,888). Furthermore, there is provided a pharmaceutical composition for inactivating HIV virus, which comprises benanomicin A or benanomicin B as active ingredient (see Japanese patent application publication "Kokai" No. 56,432/90, published 26 February 1990 and its corresponding European patent application No. 89.402315.9 filed on 21 August 1989 and corresponding U.S. patent application Ser No. 394,539 filed on 16 August 1989. The chemical structure of benanomicin A is shown by the following formula (II)

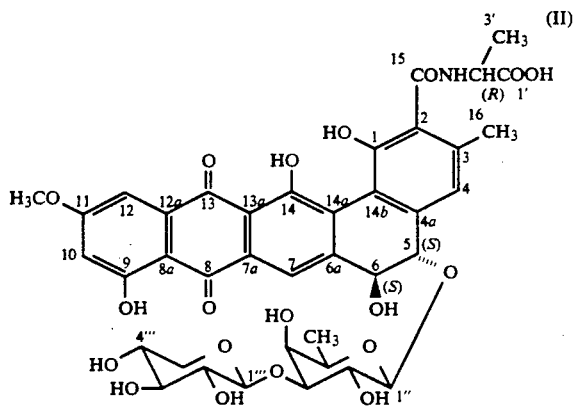

As another derivatives of benanomicins A and B, there are also earlier provided dexylosylbenanomicin A (Japanese patent application No. 248,143/89 filed on Sept. 26, 1989) and N-acetylbenanomicin B (Japanese patent application No. 4701/89, filed on Jan. 13, 1989 and its corresponding U.S. patent application Ser. No. 459,352 and corresponding European patent application No. 0.100210.5). However, benanomicins A and B, dexylosylbenanomicins A and B, as well as N-acetylbenanomicin B which are earlier provided by us in the above-mentioned earlier patent applications do not have a satisfactorily high solubility in water and, due to this, their therapeutic uses are limited to an extent. In this situation, we, the present inventors, have made researches in an attempt to provide such new derivatives of benanomicins A and B which have both the desirable antifungal activity and antiviral activity and additionally can show an improved solubility in water, as compared with the parent benanomicins A and B. As a result, we have now found that when the hydroxyl group at 4'''-position of benanomicin A is chemically converted into its sulfate ester derivative, there can be produced a new antibiotic, benanomicin A 4'''-O-sulfate or a salt thereof, which has an improved water-solubility over that of the parent benanomicin A and exhibits a useful antifungal activity and antiviral activity. We have studied the physicochemical and biological properties of benanomicin A 4'''-O-sulfate or its salts to confirm that benanomicin A 4'''-O-sulfate and a salt thereof are new substance clearly distinguishable from any of the known antibiotics. Thus, we have acomplished this invention.

Thus, an object of this invention is to provide a new antibiotic, benanomicin A 4'''-O-sulfate or a salt thereof which exhibits an antifungal activity and an antiviral activity as well as an improved solubility in water. Another object of this invention is to provide a process for the production of the new antibiotic, benanomicin A 4'''-O-sulfate and a salt thereof. Further objects of this invention will be clear from the following descriptions.

DETAILED DESCRIPTION OF THE INVENTION

According to a first aspect of this invention, therefore, there is provided a new antifungal and antiviral antibiotic, benanomicin A 4'''-O-sulfate or a salt thereof having the general formula (I)

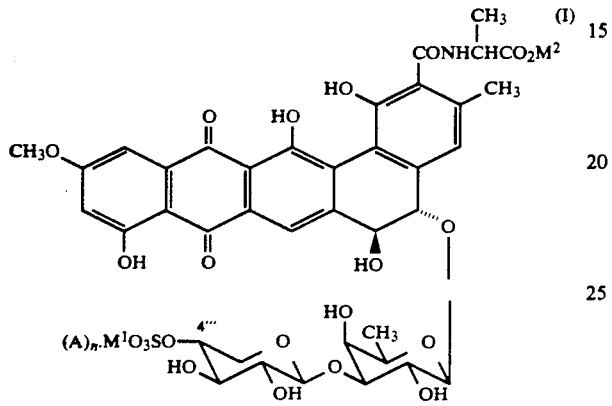

wherein $M^1$ denotes a mono-valent alkali metal atom or a di-valent alkaline earth metal atom or a hydrogen hatom and A denotes an organic base; n is zero when $M^1$ is an alkali metal atom or alkaline earth metal atom but n is 1 or zero when $M^1$ is a hydrogen atom, and $M^2$ denotes a hydrogen atom or an alkali metal atom or an alkaline earth metal atom.

More particularly, in the new benanomicin A derivative having the general formula (I) shown above according to this invention, $M^1$ and $M^2$ may independently be either a pharmaceutically acceptable alkali metal such as sodium, potassium and lithium, or a pharmaceutically acceptable alkaline earth metal such as calcium and magnesium, or hydrogen atom. The symbol A can denote a pharmaceutically acceptable organic base, including a tri-(lower)alkylamine such as triethylamine, tri-methylamine, dicyclohexyl-ethylamine; and pyridine and the like.

For example, some salts of benanomicin A 4'''-O-sulfate according to this invention have the undermentioned characteristics:

1. Physicochemical properties of some salts of benanomicin A 4'''-O-sulfate are listed below.
    (a) For benanomicin A 4'''-O-sulfate mono-pyridine addition salt of the formula (I) where $M^1 = M^2 =$ hydrogen, n = 1, A = pyridine.
    (1) Color and appearance: Dark reddish powder
    (2) Empirical formula: $C_{39}H_{40}NO_{22}S \cdot C_5H_6N$
    (3) Mass spectrometry (FAB-MS): m/z908 $(M+H)^+$ m/z906 $(M-H)^-$
    (4) Melting point: 172°-178° C. (with decomposition)
    (5) Ultraviolet and visible-ray absorption spectrum ($\lambda$mas, nm): [In water]: 237, 249(sh), 255(sh), 263(sh), 286
    (6) Infrared absorption spectrum (KBr, $cm^{-1}$): 3430, 2340, 1725, 1625, 1495, 1450, 1397, 1340, 1300, 1255, 1235, 1160, 1060, 1040, 980, (7) $^1$H-NMR spectrum (400 MHz, in DMSO-$d_6$)
    $\delta$(ppm): 1,10(3H), 1.31(3H), 2.31(3H), 3.1-3.2(2H), 3.31(1H), 3.54(1H), 3.59(1H), 3.60(1H), 3.70(1H), 3.92(1H), 3.93(3H), 3.96(1H), 4.39(1H), 4.43(1H), 4.50(1H), 4.51(1H), 4.56(1H), 4.64(1H), 6.92(1H), 7.18(1H), 7.27(1H), 8.03(2H), 8.06(1H), 8.56(1H+1H), 8.91(2H), 12.80(1H)

(8) $^{13}$C-NMR spectrum (100 MHz, in DMSO-$d_6$)
    $\delta$(ppm) 16.4, 16.9, 19.2, 47.9, 56.5, 63.5, 69.8, 70.2, 70.3, 71.8, 73.8, 74.4, 74.4, 81.6, 83.2, 104.5, 105.1, 106.9, 107.7, 110.1, 113.5, 113.6, 115.6, 125.6, 127.0, 127.6, 131.4, 134.3, 137.4, 138.1, 142.7, 145.6, 147.8, 151.0, 156.9, 164.8, 166.0, 167.0, 174.1, 185.0, 187.6

(b) For di-sodium benanomicin A 4'''-O-sulfate of the formula (I) where $M^1 = M^2 =$ sodium, and n = 0.
    (1) Color and appearance: Dark reddish powder
    (2) Empirical formula: $C_{39}H_{39}NO_{22}S \cdot 2Na$
    (3) Melting point: 231°-235° C. (with decomposition)
    (4) $^1$H-NMR spectrum (400 MHz, DMSO-$D_6$)
    $\delta$(ppm): 1.00(3H), 1.31(3H), 2.27(3H), 3.17(2H), -3.3(1H), 3.54(1H), 3.58(1H), 3.60(1H), 3.71(1H), 3.91(3H), 3.94(2H), 4.36(1H), 4.40(1H), 4.43(1H), 4.45(1H), 4.56(1H), 4.63(1H), 5.16(2H), 5.71(1H), 5.86(1H), 6.75(1H), 6.98(1H), 7.16(1H), 7.79(1H), 8.56(1H), 13.12(1H)

That the salts of benanomicin A 4'''-O-sulfate according to this invention have a high solubility in water will be demonstrated by that 100 mg or more of di-sodium benanomicin A 4'''-O-sulfate can be dissolved in 1 ml of water.

2. Antifungal activity of a salt of benanomicin A 4'''-O-sulfate is now described.

The minimum inhibitory concentrations of a salt of benanomicin A 4'''-O-sulfate against a variety of fungi were determined by a standard serial dilution method on a nutrient agar medium containing 1% glucose (pH 7.0) and are shown in Table 1 below.

TABLE 1

| Microorganism tested (fungi) | Minimum inhibitory concentrations ($\mu$g/ml) | |
|---|---|---|
| | benanomicin A 4'''-O-sulfate mono-pyridin addition salt | disodium benanomicin A 4'''-O-sulfate |
| *Candida tropicalis* F-1 | 25 | 25 |
| *Candida pseudotropicalis* F-2 | 6.25 | 6.25 |
| *Candida albicans* 3147 | 12.5 | 25 |
| *Candida* Yu-1200 | 25 | 25 |
| *Candida krusei* F-5 | 12.5 | 25 |
| *Saccharomyces cerevisiae* F-7 | 6.25 | 6.25 |
| *Cryptococcus neoformans* F-10 | 6.25 | 6.25 |
| *Cochliobolus miyabeanus* | >100 | >100 |
| *Pyricularia oryzae* | >100 | >100 |
| *Pellicularia sasakii* | 12.5 | 50 |
| *Xanthomonas citri* | 50 | >100 |
| *Xanthomonas oryzae* | >100 | >100 |
| *Aspergillus niger* F-16 | 100 | 100 |
| *Trichophyton asteroides* 429 | >100 | >100 |
| *Trichophyton mentagrophytes* F-15(883) | 100 | >100 |

3. Activity of a salt of benanomicin A 4'''-O-sulfate to inhibit infection with HIV is now tested.

Thus, the following assay tests were conducted in order to demonstrate that a salt of benanomicin A 4'''-O-sulfate has an inhibitory activity to infection of human T-cells with HIV, namely the acquired human immunodeficiency syndrome virus. The procedure for these assay tests is as follows:

Effects of benanomicin A 4'''-O-sulfate monopyridine addition salt inhibitory against infection of human T-cells with HIV were examined in a similar manner to the assay methods described in the "Proc. Natl. Acad. Sci. USA," 80, 6061–6065 (1983); "J. Antibiot.", 40, 1077–1078, (1987); and "J. Antibiot.", 42, 344–346, (1989).

About $1 \times 10^5$ cells/ml of MT-4 cells (human T-cell line) in phosphate buffered saline were seeded into Costar 48-well plates in an amount of 0.5 ml/well. Each well was added with 50 μl of a solution of benanomicin A 4'''-O-sulfate mono-pyridin addition salt [dissolved at a concentration of 10 mg/ml in dimethyl sulfoxide (DMSO) and then diluted with phosphate buffered saline to varying concentrations of the test compound]. Two hours later, MT-4 cells were infected with HIV (1,000–10,000 plaque-forming units) in each well. The plates were incubated for 4 days at 37° C. under 5% $CO_2$. The MT-4 cells were smeared onto slide glasses, dried and fixed with acetone. The presence of HIV antigen-positive cells were detected by the indirect immunofluoroescent assay [Y. Hinuma et al., "Proc. Natl. Acad. Sci. USA," 78, 6476–6480, (1981)]. Thus, cell smears were treated at 37° C. for 30 minutes with serum of AIDS patient as the first antibody. After washing with phosphate buffered saline, the cells were further treated at 37° C. for 30 minutes with fluorescent isothiocyanate(FITC)-conjugated rabbit anti-human immunoglobulin serum (Cappel Laboratories, Cochranville, Penna, USA) as the second antibody. After the cell smears were then washed with phosphate buffered saline and covered with a cover glass, the cells were examined under a fluorescence microscope. Percentages of the number of viral antigen-positive cells (namely, immunofluorescent cells where the HIV-associated antigens were expressed) in the total cells were calculated.

Furthermore, cytotoxicity of benanomicin A 4'''-O-sulfate mono-pyridine addition salt to the MT-4 cells was estimated by incubating the MT-4 cells at varying concentrations of the benanomicin A derivative under test and in the absence of HIV but in the same manner of incubation and under the same conditions of incubation of MT-4 cells as those employed in the above-mentioned test procedure of assaying the activity of benanomicin A 4-O-sulfate mono-pyridine addition salt to inhibit infection of T-cells with HIV.

The results of the above tests of assaying the inhibitory activity of the tested benanomicin A derivative to the HIV-infection as well as the tests of estimating the cytotoxicity of the same compound are shown in Table 2 below.

TABLE 2

| Concentration of test compound (μg/ml) | Percentage of the number of viral antigen-positive cells (%) | Cyto- toxicity |
| --- | --- | --- |
| 100 | <0.1 | ± |
| 30 | 15 | — |
| 10 | 30 | — |
| 3 | 65 | — |
| 0 | >65 | — |

TABLE 2-continued

| Concentration of test compound (μg/ml) | Percentage of the number of viral antigen-positive cells (%) | Cyto- toxicity |
| --- | --- | --- |

As is apparent from the test results of the above Table 2, it has been confirmed that benanomicin A 4'''-O-sulfate mono-pyridine addition salt under test is free of the cytotoxicity at its concentration of 10 μg/ml and can significantly reduce the number of viral antigen-positive cells. Accordingly, it has been confirmed that benanomicin A 4'''-O-sulfate mono-pyridine addition salt has a high activity to inhibit infection of human T-cells with HIV and hence shows an antiviral activity against HIV.

4. Acute toxicity of a salt of benanomicin A 4'''-O-sulfate is next described.

When acute toxicity of disodium benanomicin A 4'''-O-sulfate according to this invention was tested in a mammalian animal upon intravenous administration, it was revealed that the new compound of this invention is of a very low acute toxicity. Thus, in an acute toxicity test where disodium benanomicin A 4'''-O-sulfate was administered via intravenous route to ICR mice (female, 4-week old, body weight of 19 to 21 g), the mice tolerated a dosage of 500 mg/kg of this disodium salt.

In a second aspect of this invention, there is provided an antifungal composition for therapeutic treatment of a fungal infection in a mammalian animal, including human, which comprises an antifungally effective amount of a benanomicin A 4'''-O-sulfate or a salt thereof having the formula (I) as defined hereinbefore, as active ingredient, in association with a pharmaceutically acceptable solid or liquid carrier.

In a third aspect of this invention, there is provided an antiviral composition for therapeutic treatment of viral infection in a mammalian animal, including human, which comprises an antivirally effective amount of benanomicin A 4'''-O-sulfate or a salt thereof having the formula (I) as active ingredient, in association with a solid or liquid carrier for the active ingredient.

According to a further aspect of this invention, there is provided a method for inhibiting a virus, particularly acquired human immunodeficiency syndrome virus, which comprises treating the virus with benanomicin A 4'''-O-sulfate or a salt thereof having the formula (I) in an amount sufficient to inactivate the virus.

The pharmaceutical antifungal or antiviral composition containing the new compound of the formula (I) according to this invention as the active ingredient may be formulated in a known manner into a conventional formulation for administration, for example, powder, granules, tablets, pills and capsules for oral administration, as well as intravenously, intramuscularly or subcutaneously injectable solution, and suppositories, using a pharmaceutically acceptable solid or liquid carrier which is suitable for the intended formulation.

In general, the new compound of the formula (I) according to this invention can be administered either orally or parenterally upon its actual administration in the form of an antifungal or antiviral composition.

When the active ingredient compound of the formula (I) according to this invention is given either as the antifungal agent or as the antiviral agent against HIV, it can be administered alone or it can be administered in the form of an injection, oral preparation, suppository or the like containing an excipient or carrier as mixed together. Any pharmaceutically acceptable excipient and carrier are available for that purpose. The nature and quantity of the carrier used may vary depending on the administration route and manner. For example, water, ethanol, an animal or vegetable oil such as soybean oil, sesame oil or mineral oil, or a synthetic oil may be used as a liquid carrier. Suitable solid carriers include, for example, a sugar such as maltose or sucrose, an amino acid, a cellulose derivative such as hydroxypropylcellulose, a polysaccharide such as cyclodextrin, a salt of an organic acid such as magnesium stearate, or the like. In the case of the injections, it is generally preferable that the liquid medium of the injections comprises physiological saline, a buffered solution, an aqueous solution of a sugar such as glucose, inositol or mannitol, or a glycol such as ethylene glycol or polyethylene glycol. It is also feasible to formulate a lyophilized preparation containing the benanomicin A derivative of the formula (I) as the active ingredient mixed along with an excipient, e.g., a sugar such as inositol, mannitol, glucose, mannose, maltose or sucrose or an amino acid such as phenylalanine. Upon administration, such lyophilized preparation may be dissolved in a suitable solvent for injection, for example, sterilized water or an intravenously-administerable liquid such as physiological saline, aqueous solution of glucose, an aqueous solution of electrolytes or an aqueous solution of amino acid.

Although the proportion of the benanomicin A derivative of the formula (I) present in the formulated composition may widely vary from one preparation to another preparation, it may generally be in a range of 0.1-100% by weight. In the case of an injection, for example, it is generally desirable that the injectionable solution contains the compound of the formula (I) as active ingredient at a concentration of 0.1-20% by weight. For oral administration, the compound of the formula (I) may be formulated into tablets, capsules, a powder, granules in mixture with a solid carrier or it may also be formulated into a solution, a dry syrup or the like in combination with a liquid carrier. In capsules, tablets, granules or a powder, the proportion of the benanomicin A derivative of the formula (I) present therein may generally be in a range of about 3-100%, preferably 10-100% by weight, with the balance being a carrier or carriers.

The dosage of the benanomicin A derivative of the formula (I) may suitably be determined in account of the age, body weight, symptone of patients and the therapeutic purpose as intended. The therapeutic, i.e., effective dosage of the benanomicin A derivative of the formula (I) may be generally in a range of 1-50 mg/kg/day for the parenteral administration and in a range of 5-100 mg/kg/day for the oral administration. This dosage can be administered either continuously or intermittently as long as the total dosage does not exceed such a specific level that was decided in view of results of animal tests and various circumstances. Similarly, the total dosage given in the parenteral administration may, of course, vary suitably depending on the way of administration, conditions of the patient or animal under treatment, for example, the age, body weight, sex, sensitivity, foods or feed, administration time, administration route, drugs administered concurrently, conditions of the patient and disease. The suitable dosage and administration frequency of the benanomicin A derivative of the formula (I) under given conditions must be determined by an expert physician through the tests of determining optimal dosage and in light of the above guidelines. These requirements for administration should also applies to the oral administration of the benanomicin A derivative of the formula (I) according to this invention.

In another aspect of this invention, there is provided a process for the production of an antifungal and antiviral antibiotic, benanomicin A 4'''-O-sulfate or a salt thereof having the general formula (I) as defined hereinbefore, which comprises converting chemically the antibiotic, benanomicin A to give benanomicin A 4'''-O-sulfate or a salt thereof.

The method for preparing the starting benanomicin A is described in the specification of the aforesaid European patent application publication No. 0 315 147 A2, but the preparation of benanomicin A is briefly illustrated hereinafter with reference to Referential Examples 1 to 2.

In carrying out the production process of this invention, the reaction for chemical conversion of benanomicin A into its 4'''-O-sulfate ester derivative or a salt thereof may be effected by reacting benanomicin A in its unprotected form either with sulfur trioxide, namely sulfuric acid anhydride, or with a complex of sulfur trioxide with an organic base in a dry reaction medium formed of an anhydrous organic solvent such as N,N-dimethylformamide and pyridine, at a temperature of 20° to 50° C. Dry pyridine is preferable to be used as the reaction medium. When a complex of sulfur trioxide with an organic base is used as the reagent, the organic base component for forming the sulfur trioxide-organic base complex may be a tri-(lower)alkylamine, a dicycloalkyl-(lower)alkylamine or pyridine. Thus, a complex of sulfur trioxide with an organic base which is available as the reagent may be such a complex of sulfur trioxide with a trialkylamine represented by the following formula

 (III)

wherein $R^1$, $R^2$ and $R^3$ are each a lower alkyl group, especially a $(C_1-C_4)$alkyl group such as methyl, ethyl and propyl, or alternatively $R^1$ is a lower alkyl group and both $R^2$ and $R^3$ are each a cycloalkyl group, especially a $(C_3-C_6)$ cycloalkyl group such as cyclopentyl and cyclohexyl, or such a complex of sulfur trioxide with pyridine represented by the following formula

 (IV)

When the benanomicin A having it hydroxyl groups unprotected is reacted with a complex of sulfur trioxide with a trialkylamine or pyridine in an equimolor proportion or in a slight excess of the sulfur trioxide-organic base complex, there is generally formed the corresponding trialkylamine salt or pyridine salt of benanomicin A 4'''-O-sulfate represented by the formula

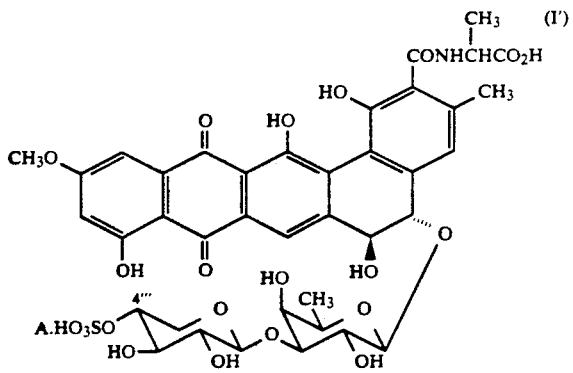

wherein A denotes the trialkylamine or pyridine, as long as the reaction is conducted in the reaction medium formed of an organic solvent other than pyridine. On the other hand, when the unprotected benanomicin A is reacted with a complex of sulfur trioxide with a trialkylamine in a reaction medium formed of dry pyridine, there are once produced in a mixture both of the trialkylamine salt and the pyridine salt of benanomicin A 4'''-O-sulfate according to the above formula (I'), and the trialkylamine salt as once formed of benanomicin A 4'''-O-sulfate is then further reacted with pyridine present in the reaction medium so as to be converted into the pyridine addition salt of benanomicin A 4'''-O-sulfate. Consequentially, when the reaction of benanomicin A with a complex of sulfur trioxide and pyridine or even with a complex of sulfur trioxide and a trialkylamine is effected in a reaction medium formed of dry pyridine to a completion, the reaction product can be obtained wholly in the form of the mono-pyridine addition salt of benanomicin A 4'''-O-sulfate. Thus, a mono-pyridine addition salt of benanomicin A 4'''-O-sulfate as one example of the new benanomicin A derivatives having the formula (I) above may be produced by reacting unprotected benanomicin A with a complex of sulfur trioxide and a trialkylamine in equimolar or substantial equimolar proportions within a reaction medium formed of dry pyridine, thereby producing a trialkylamine addition salt of benanomicin A 4'''-O-sulfate and the mono-pyridine addition salt of benanomicin A 4'''-O-sulfate according to the above formula (I') in mixture, and then further reacting the trialkylamine addition salt of benanomicin A 4'''-O-sulfate as formed with a further amount of pyridine, without effecting isolation of said trialkylamine addition salt, whereby the trialkylamine addition salt of benanomicin A 4'''-O-sulfate is converted into the mono-pyridine addition salt of benanomicin A 4'''-O-sulfate.

If necessary, the trialkylamine addition salt or pyridine addition salt of benanomicin A 4'''-O-sulfate which has been obtained as the reaction product may be purified by subjecting it to a liquid-liquid distribution chromatography with developed with conventional mixed solvents of two liquid phases, for example, a solvent mixture of 1-butanol and water, a solvent mixture of 1-butanol, water and acetic acid, or a solvent mixture of 1-butanol, water and pyridine, and the like.

When the trialkylamine addition salt or pyridine addition salt of benanomicin A 4'''-O-sulfate as obtained through the above-mentioned reaction procedures is then reacted with a carbonate, a hydrogen carbonate or a hydroxide of an alkali metal or an alkaline earth metal in water, there may be formed the corresponding di-alkali metal or alkaline earth metal benanomicin A 4'''-O-sulfate having the formula (I) in the metal salt form where n is zero.

In a particular embodiment of the process of this invention, therefore, the mono-pyridine addition salt of benanomicin A 4'''-O-sulfate may be produced by reacting benanomicin A (in its unprotected form) with a complex of sulfur trioxide with a trialkylamine in a reaction medium consisting of dry pyridine, thereby producing a trialkylamine addition salt of benanomicin A 4'''-O-sulfate and a mono-pyridine addition salt of benanomicin A 4'''-O-sulfate in mixture through interaction as effected between benanomicin A, the sulfur trioxide-trialkylamine complex and pyridine, followed by further reacting said trialkylamine addition salt of benanomicin A 4'''-O-sulfate with pyridine to form the mono-pyridine addition salt of benanomicin A 4'''-O-sulfate as a final reaction product.

In another particular embodiment, a di-alkali metal salt or an alkaline earth metal salt of benanomicin A 4'''-O-sulfate may be produced by reacting benanomicin A with a complex of sulfur trioxide with a trialkylamine in a reaction medium consisting essentially of pyridine, thereby producing a trialkylamine addition salt of benanomicin A 4'''-O-sulfate and a pyridine addition salt of benanomicin A 4'''-O-sulfate in mixture, further reacting said trialkylamine addition salt of benanomicin A 4'''-O-sulfate with pyridine to produce a mono-pyridine addition salt of benanomicin A 4'''-O-sulfate, followed by recovering and then reacting the resulting mono-pyridine addition salt of benanomicin A 4'''-O-sulfate with an alkali metal carbonate or hydroxide or an alkaline earth metal carbonate or hydroxide in water, to form the di-alkali metal or alkaline earth metal salt of benanomicin A 4'''-O-sulfate.

Since benanomicin A which is used as a starting material for the production of the benanomicin A derivative of the formula (I) is an antibiotic which is produced by cultivation of a new microorganism, MH193-16F4 strain, the fermentative production of this antibiotic is described hereinafter.

The production of benanomicin A may be carried out by inoculating the MH193-16F4 strain of actinomycete to a culture medium containing such nutrient sources which can be utilized by ordinary microorganisms, and then incubating said benanomicin-producing strain under aerobic conditions. Benanomicin A is produced together with benanomicin B and they are accumulated primarily in the culture broth. Benanomicins A and B may be recovered from the resulting culture, especially from the culture broth or its filtrate.

The nutrient sources available in the culture medium to be used may be any of the conventional carbon and nitrogen sources which have been useful as nutrient sources for the cultivation of known strains of actinomycete. For example, the assimilable nitrogen sources may include soybean meal, peptone, meat extract, corn steep liquor, cotton seed meal, peanut meal, dry yeast, yeast extract, NZ-amine, casein, sodium nitrate, ammonium sulfate and ammonium nitrate which are commercially available. The assimilable carbon sources may include glycerin, sucrose, starch, glucose, galactose, maltose, dextrin, lactose, molasses, soybean oil, fats and amino acids, which are commercially available. The culture medium may also contain inorganic salts such as sodium chloride, phosphates, calcium carbonate, magnesium sulfate, cobalt chloride and manganese chloride.

In addition, trace amounts of metal salts, and one or more of animal, vegetable or mineral oils can also be added.

Liquid cultivation methpd is preferred for the production of benanomicins A and B in a large scale. The cultivation temperature may be chosen within the range of the temperatures at which the benanomycins-producing microorganism can grow and can produce benanomicins A and B. The cultivation temperature may generally be at 20°-40° C., preferably at 25°-37° C.

For recovery of benanomicins A and B from the resulting culture of the microorganism capable of producing benanomicins A and B, benanomycins A and B can be extracted from the culture or the culture broth filtrate and then purified by using conventional methods for recovery and purification, for example, solvent extraction, ion-exchange resin method, adsorptive or partition column chromatography, gel filtration, dialysis, precipitation and the like, either singly or in combination. For example, benanomicins A and B can be recovered from the incubated mycelial cake by extacting with acetone-water or methanol-water. On the other hand, benanomicins A and B which have been produced and accumulated in the culture broth or the filtrate can be adsorbed on an adsorbent such as a microporous non-ionic resinous adsorbent, for example, "Diaion" HP-20 (trade name; synthetic resinous adsorbent produced by Mitsubishi Kasei Corporation, Japan). In addition, when the culture broth or the broth filtrate is extracted with an organic solvent immiscible with water, e.g., butanol, ethyl acetate or the like, benanomicin A and B substances are extracted in the organic solvent phase.

For the production of benanomicins A and B, it is preferred that the MH193-16F4 strain is cultivated in a culture medium under aerobic conditions at a temperature of 25° to 37° C., preferably for 3 to 10 days, to produce and accumulate benanomicin A and benanomicin B in the resulting culture broth, the culture broth is filtered, and the resultant culture broth filtrate is passed through a column of an adsorbent to effect the adsorption of benanomicin A and benanomicin B by the adsorbent, and benanomicin A and benanomicin B are separately recovered by chromatographically eluting the column of the adsorbent containing benanomicins A and B adsorbed therein.

For mutual isolation and further purification of benanomicins A and B, chromatographic method with use of an adsorbent such as silica gel ("WAKOGEL C-300", trade name, product of Wako Pure Chemical Industries, Ltd.), and alumina or a gel-filtration agent "Sephadex LH-20" (trade name; product of Pharmacia AB), or the like may be made suitably.

Benanomicins A and B as produced in the culture as described above can be isolated as benanomicins A and B as such in their free form.

Incidentally, the MH193-16F4 strain has been deposited in an authorized Japanese depository "Fermentation Research Institute", Agency of Industrial Science and Technology, Ministry of International Trade and Industry, Japanese Government, under the deposit number FERM P-9529 since Aug. 21, 1987. The MH193-16F4 strain has now been deposited in the "Fermentation Research Institute" in terms of the Budapest Treaty under the deposit number "FERM BP-2051". This Japanese depository locates in Tsukuba-city, Ibaragi-ken, Japan.

The following Referential Examples 1 to 2 illustrate the fermentative production of benanomicins A and B.

REFERENTIAL EXAMPLE 1

A loopful quantity of the MH193-16F4 strain (identified as FERM BP-2051), which had been incubated in a slant agar medium, was inoculated into 80 ml of a liquid culture medium comprising 1.0% starch and 3.0% soybean meal (pH 7.0 before the sterilization) which was placed in a Sakaguchi's flask of 500 ml-capacity. The inoculated culture medium was incubated at 28° C. for 3 days under rotatory shaking (135 rpm.) to provide a first seed culture. The first seed culture obtained was inoculated in 3 ml-portions into 80 ml-portions of the liquid culture medium having the same composition as above, which were separately placed in many Sakaguchi's flasks. The inoculated culture media were incubated for 3 days under the same incubation conditions as above, to give the second seed culture. The resultant second seed culture ( 2 liters) was then inoculated to a culture medium (50 liters) of the same composition as above which had been sterilized at 120° C. for 15 minutes and was placed in a tank-fermentor of 100 l-capacity. The so inoculated culture medium was then cultured at 28° C. for 2 days under aeration at a rate of 50 l of air per minute and under agitation at 200 rpm. to effect the submerged cultivation of the MH193- 16F4 strain under aerobic conditions and obtain a third seed culture. The resultant third seed culture (12 liters) was inoculated into a productive culture medium (300 liters) comprising 2.0% of glycerin, 1.5% of soybean meal (available commercially under a tradename "Esusan Meat", a product of Ajinomoto Co. Ltd., Japan), 0.0025% of $K_2HPO_4$, 0.1125% of $KH_2PO_4$, 0.005% of $CoCl_2 19$ $6H_2O$, 0.03% of a silicone oil "KM72" (an antifoaming agent, a trade name.of a product of Shinetsu Chemicals Co. Ltd., Japan) and 0.01% of a surfactant "Adekanol" (a trade name, product of Asahi Denka Kogyo Co. Ltd., Japan) which had preliminarily been sterilized at 125° C. for 30 minutes and was placed in a tank-fermentor of 570 l-capacity. The cultivation was conducted at 28° C. for 7 days under agitation at 300 rpm. and under aeration at a rate of 150 l of air per minute for the first 24 hours of the cultivation and then at a rate of 300 l of air per minute after 24 hours of cultivation. After the completed cultivation, the culture broth obtained was mixed with diatomaceous earth as a filtration-aid and then filtered to give 250 l of the culture broth filtrate (pH 6.0).

REFERENTIAL EXAMPLE 2

The culture broth filtrate (250 l) obtained in the above Referential Example 1.was passed through a column of 15 l of a microporous non-ionic adsorbent resin "Diaion" HP-20 to effect the adsorption of the active substances by the adsorbent. After the adsorbent column was washed with 100 l of water and with 45 l of 50% aqueous methanol, the adsorbent column was eluted with 45 l of 70% aqueous methanol and then with 90 l of dry methanol, and the eluate was collected as the first fraction (53 l) and the second fraction (38 l) which contained benanomicin A, as well as the third fraction (27 l) which contained benanomicin B, with the eluate being collected in fractions. The first fraction containing benanomicin A was concentrated to 3 l under reduced pressure, followed by adjustment to pH 3.5 with dilute hydrochloric acid to deposit a precipitate of a red color. The precipitate was collected by filtration and then dried under reduced pressure, whereby 152 g of a crude brown powder mainly comprising benanomicin A was obtained.

The crude powder (150 g) was dissolved in 600 ml of dimethylformamide. After saturation of the resultant solution with water vapor at room temperature for 3 days in a desiccator, a crystalline precipitate was deposited. The precipitate was collected by filtration and then dried under reduced pressure, thereby obtaining 29 g of bananomicin A-dimethylformamide solvate. The second fraction of the eluate was processed in the same way as the first fraction, thereby obtaining 14 g of benanomicin A-dimethylformamide solvate.

One gram of the benanomicin A-dimethylformamide solvate as obtained from said first fraction was dissolved in dimethyl sulfoxide (5 ml). The resultant solution was added dropwise under stirring into 300 ml of methanol, followed by stirring for 10 minutes to deposit a precipitate of a reddish brown color. The precipitate was filtered out and then dried under reduced pressure, to afford 935 mg of a purified benanomicin A as reddish brown powder.

This invention is now illustrated with reference to the following Examples, to which this invention is not limited in any way. Thus, it is feasible for the skilled in the art to contemplate and perform the process of producing the new compound of the formula (I) in different ways. Accordingly, this invention embraces any modification of the procedures of the following Examples.

EXAMPLE 1

Benanomicin A (251 mg) was dissolved in 5 ml of dry pyridine and the resulting solution was added with 84 mg of a complex of sulfur trioxide with trimethylamine [of the formula $SO_3.N(CH_3)_3$]. The mixture obtained was stirred at 50° C. for 2 hours to effect the reaction where benanomicin A was reacted with the sulfure trioxidetrimethylamine complex in solution in pyridine. The reaction solution so obtained was then concentrated to dryness under a reduced pressure, and the resulting solid residue comprising both a trimethylamine addition salt of benanomicin A 4'''-O-sulfate as formed and a pyridine addition salt of benanomicin A 4'''-O-sulfate as formed was dissolved in aqueous pyridine. The resulting solution in the aqueous pyridine was again concentrated to dryness under a reduced pressure. This cycle comprising the dissolution of the residue into aqueous pyridine and the concentration of the solution to dryness under a reduced pressure was repeated further three times. The solid residue finally obtained was subjected to a counter-current partition chromatography (CPC)(using a chromatographic apparatus of "Model NMF" as produced by Sanki Engineering Co., Japan). The partition solvent used was a mixture of 1-butanol, water and pyridine (100:100:2, by volume). In this CPC. method, a cell of 880 ml-capacity was used while one litre of the mobile layer (the upper layer) was eluted out, followed by reversed elution of the lower layer. The fraction of the eluate which was containing the desired pyridine addition salt of benanomicin A 4'''-O-sulfate was collected and concentrated to dryness under a reduced pressure. Thus, a mono-pyridine addition salt of benanomicin A 4'''-O-sulfate was obtained as a dark reddish powder in a yield of 60 mg.

EXAMPLE 2

The mono-pyridine addition salt (10.1 mg) of benanomicin A 4'''-O-sulfate as obtained in Example 1 above was suspended in 0.5 ml of water with a part of the benanomicin A derivative being dissolved but another parts remaining undissolved in water. To the resulting aqueous suspension was added 1.1 mg of sodium carbonate, followed by stirring the mixture until the undissolved parts of the benanomicin A derivative were dissolved to give a completely clear aqueous solution. This aqueous solution was concentrated to dryness under a reduced pressure, affording 10 mg of di-sodium benanomicin A 4'''-O-sulfate (in the form of the mono-sodium sulfate and mono-sodium carboxylate)as a dark reddish powder.

We claim:

1. An antibiotic, benanomicin A 4'''-O-sulfate or a salt thereof having formula (I)

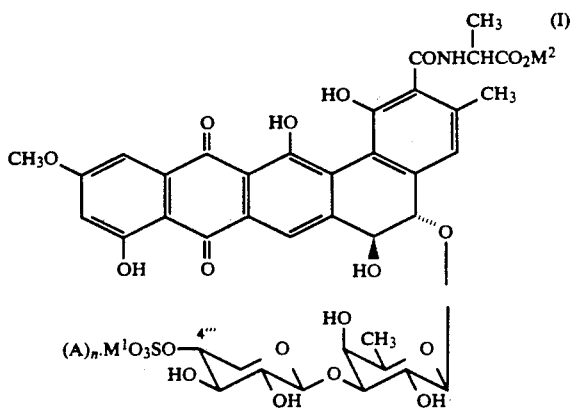

where $M^1$ denotes a mono-valent alkali metal atom or a di-valent alkaline earth metal atom or a hydrogen atom and A denots a tri (lower) alkylamine or pyridine; n is zero when $M^1$ is an alkali metal atom or alkaline arth metal atom but n is 1 or zero when $M^1$ is a hydrogen atom, and $M^2$ denotes a hydrogen atom or an alkali metal atom or an alkaline earth metal atom.

2. The antibiotic as claimed in claim 1, where $M^1$ and $M^2$ each are a hydrogen atom, n is 1 and A is pyridine, and which is namely benanomicin A 4'''-O-sulfate monopyridine addition salt.

3. The antibiotic as claimed in claim 1, where $M^1$ and $M^2$ each are a sodium atom and n is zero, and which is namely di-sodium benanomicin A 4'''-O-sulfate.

4. An antifungal and antiviral composition which comprises a therapeutically effective amount of benanomicin A 4'''-O-sulfate or a salt thereof as claimed in claim 1, as active ingredient, in association with a pharmaceutically acceptable solid or liquid carrier.

5. A method for inhibiting acquired human immunodeficiency syndrome virus in vitro which comprises treating the virus with benanomicin A 4'''-O-sulfate or a salt thereof as claimed in claim 1, in an amount sufficient to inhibit the virus.

* * * * *